US009090868B2

(12) United States Patent
Mace et al.

(10) Patent No.: US 9,090,868 B2
(45) Date of Patent: Jul. 28, 2015

(54) ALGINATE HYDROGEL FIBERS AND RELATED MATERIALS

(75) Inventors: Charles R. Mace, Auburn, NY (US); Jabulani Barber, Fair Oaks, CA (US); Anna Laromaine Sagué, Cambridge, MA (US); George M. Whitesides, Newton, MA (US); Rebecca Cademartiri, Somerville, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 0 days.

(21) Appl. No.: 13/808,887

(22) PCT Filed: Jul. 12, 2011

(86) PCT No.: PCT/US2011/043718
§ 371 (c)(1),
(2), (4) Date: Aug. 15, 2013

(87) PCT Pub. No.: WO2012/009363
PCT Pub. Date: Jan. 19, 2012

(65) Prior Publication Data
US 2013/0316387 A1 Nov. 28, 2013

Related U.S. Application Data

(60) Provisional application No. 61/363,457, filed on Jul. 12, 2010.

(51) Int. Cl.
*C12N 5/00* (2006.01)

(52) U.S. Cl.
CPC ............ *C12N 5/0062* (2013.01); *C12N 5/0068* (2013.01); *C12N 2533/30* (2013.01); *C12N 2533/56* (2013.01); *C12N 2533/74* (2013.01)

(58) Field of Classification Search
CPC ............ C12N 5/0062; C12N 2533/74; C12N 2533/56; C12N 5/0068; C12N 2533/30
See application file for complete search history.

(56) References Cited

U.S. PATENT DOCUMENTS

| 2,420,308 A | 5/1947 | Gates et al. |
| 2,423,075 A | 6/1947 | Hall |

(Continued)

FOREIGN PATENT DOCUMENTS

| CN | 101187092 | 5/2008 |
| JP | 61174499 | 8/1986 |

(Continued)

OTHER PUBLICATIONS

Lawson et al., Adhesion and Growth of Bone Marrow Stromal Cells on Modified Alginate Hydrogels, Tissue Engineering, vol. 10, No. 9/10, 2004.*

(Continued)

*Primary Examiner* — Karen Cochrane Carlson
*Assistant Examiner* — Jennifer M.H. Tichy
(74) *Attorney, Agent, or Firm* — Wilmer Cutler Pickering Hale and Dorr LLP

(57) ABSTRACT

Alginate hydrogel fibers and related materials as well as methods for preparing such materials are provided. An alginate hydrogel fiber includes water in an amount of more than about 92% by weight of the fiber and a cross-linked alginate in an amount of about 0.1% to about 8% by weight of the fiber, wherein the cross-link is a cation. An alginate hydrogel paper includes one or more alginate hydrogel fibers, which form a non-woven matrix. Three-dimensional cellular arrays are also provided, wherein the alginate hydrogel making up the alginate paper is substantially index-matched with a predetermined culture medium. A method for making alginate hydrogel fiber and a method for index-matching alginate hydrogel paper with culture medium are provided. A kit for conducting biochemical, diagnostic, cellular, and/or non-cellular analysis comprises alginate hydrogel paper index-matched to culture medium.

14 Claims, 4 Drawing Sheets

(56) References Cited

U.S. PATENT DOCUMENTS

| | | | |
|---|---|---|---|
| 2,600,504 | A | 6/1952 | Johnson et al. |
| 4,104,115 | A | 8/1978 | Prouse et al. |
| 4,744,830 | A | 5/1988 | Kobayashi et al. |
| 2002/0128346 | A1* | 9/2002 | Domschke et al. ........... 523/113 |
| 2009/0087469 | A1 | 4/2009 | Zhang et al. |

FOREIGN PATENT DOCUMENTS

| | | | | |
|---|---|---|---|---|
| JP | 2259111 | | 10/1990 | |
| JP | 9279462 | | 10/1997 | |
| WO | WO 2009/120963 | * | 9/2009 | ............. G01N 33/48 |
| WO | WO-2009120693 A2 | | 10/2009 | |

OTHER PUBLICATIONS

Bracher, Paul J. et al. "Heterogeneous Films of Ionotropic Hydrogels Fabricated from Delivery Templates of Patterned Paper." Published in ACS Appl. Mater. Interfaces, vol. 1, No. 8, Jan. 1, 2009, pp. 1807-1812, accessed through NIH Public Access, 12 pages.
Crow, B.B. et al. "Release of Bovine Serum Albumin from a hydrogel-cored Biodegradable Ploymer Fiber." Biopolymers. vol. 81, No. 6, Apr. 15, 2006, pp. 419-427.
Heywood, Hannah K. et al. "Cellular Utilization Determines Viability and Matrix Distribution Profiles in Chondrocyte-seeded Alginate Constructs." Tissue Engineering, vol. 10, No. 9-10, Sep. 1, 2004, pp. 1467-1479.
Hou, et al., "Novel Surface Entrapment Process for the Incorporation of Bioactive Molecules within Preformed Alginate Fibers", Biomacromolecules, 6(2):734-740, Mar. 2005, 7 pages.
International Search Report and Written Opinion for International Application No. PCT/US2011/043718 mailed Oct. 31, 2011, 17 pages.
Kearns, V. et al. "Silk-based Biomaterials for Tissue Engineering." Topics in Tissue Engineering, vol. 4, No Month Listed 2008, pp. 1-19.
Kobayashi, et al., "Manufacture and Physical Properties of Alginate Fiber Papers as an Analysis Model of Cellulosic Fiber Papers", Journal of Applied Polymer Science, 31(6):1735-1747, May 5, 1986, 13 pages.
Kuo, Catherine K. et al. "Maintaining Dimensions and Mechanical Properties of Ionically Crosslinked Alginate Hydrogel Scaffolds In Vitro." Journal of Biomedical Materials Research Part A., vol. 84A, No. 4, Mar. 15, 2008, pp. 899-907.
Lee et al. "Integration of Layered Chondrocyte-seeded Hydrogel Scaffolds." Biomaterials, Elsever Science Publishers BV, Barking, Great Britain, vol. 28, No. 19, Apr. 14, 2007, pp. 2987-2993.
Lee et al. "Regulating in Vivo Calcification of Alginate Microbeads." Biomaterials, Elsevier Science Publishers, BV, Barking, Great Britain, vol. 31, No. 18, Jun. 1, 2010, pp. 4926-4934.
Derda et al. "Paper-supported 3D Cell Culture for Tissue-based Bioassays." Proceedings of the National Academy of Sciences of USA, Academy of Science, Washington, DC, vol. 106, No. 44, Nov. 3, 2009, pp. 18457-18462.
Safley, Susan et al. "Biocompatibility and Immune Acceptance of Adult Porcine Islets Transplanted Intraperitoneally in Diabetic NOD Mice in Calcium Alginate Poly-L-lysine Microcapsules Versus Barium Alginate Microcapsules without Poly-L-lysine." Journal of Diabetes Science and Technology, Sep. 2008, pp. 760-767.
Wan, Leo Q. et al. "Calcium Concentration Effects on the Mechanical and Biochemical Properties of Chondrocyte-Alginate Constructs." Cellular and Molecular Bioengineering, vol. 1, No. 1, Mar. 1, 2008, pp. 93-102.
Zhang et al. "An Ionically Crosslinked Hydrogel Containing Vancomycin Coating on a Porous Scaffold for Drug Delivery and Cell Culture." International Journal of Pharmaceutics, Elsevier BV, NL, vol. 353, No. 1-2, Nov. 21, 2007. pp. 74-87.
Zimmermann, et al., "Physical and Biological Properties of Barium Cross-Linked Alginate Membranes", Biomaterials, 28(7):1327-1345, Mar. 2007, 19 pages.

* cited by examiner

ALGINATE HYDROGEL FIBERS AND RELATED MATERIALS

CROSS REFERENCE TO RELATED APPLICATIONS

This application is the National Stage of International Application No. PCT/US2011/043718, filed Jul. 12, 2011, designating the United States and entitled "Alginate Hydrogel Fibers and Related Materials," which claims the benefit of priority under 35 U.S.C. §119(e) to U.S. Provisional Application No. 61/363,457, filed Jul. 12, 2010, the entire contents of which are hereby incorporated by reference herein.

INCORPORATION BY REFERENCE

All patents, patent applications and publications cited herein are hereby incorporated by reference in their entirety in order to more fully describe the state of the art as known to those skilled therein as of the date of the invention described herein.

BACKGROUND

The technology described herein relates to polymeric fibers and related materials and methods for preparing and using such materials.

Polymeric fibers can be used for a broad spectrum of biological and medical applications. They can be used as support for three-dimensional cell culture and tissue-based bioassays. Cells in vivo reside in an organized three-dimensional environment as part of tissue and organ structures. Conventional two-dimensional cell culture approaches cannot recreate the structure of living tissues.

The development of three-dimensional cell culture can more accurately mimic tissues and organ structures. However, the need to control multiple chemical and physical properties of the cell matrix makes current three-dimensional cell culture strategies labor-intensive and difficult to reproduce.

SUMMARY

This disclosure describes alginate hydrogel fibers, papers, diagnostics and cell culturing devices and methods for preparing and using such materials.

In one aspect, an alginate hydrogel fiber comprises:
water in an amount of more than about 92% by weight of the fiber; and
a cross-linked alginate in an amount of about 0.1% to about 8% by weight of the fiber, wherein the cross-link comprises a divalent or multivalent cation.

In one or more embodiments, the alginate hydrogel fiber comprises alginate in an amount of from about 0.5% to about 2% by weight of the fiber.

In one or more embodiments, alginate hydrogel fiber also includes additives. The additives can be selected from the group consisting of salts, peptides, organic molecules, drugs, signaling molecules, antibiotics, vitamins and small molecules and mixtures thereof.

In one or more embodiments, the diameter of the alginate hydrogel fiber ranges from about 0.1 mm to about 1 mm.

In one or more embodiments, the length of the alginate hydrogel fiber ranges from the order of centimeters to kilometers. In another embodiment, the fiber ranges from about 5 m to about 15 m.

In one or more embodiments, the cation cross-linker is selected from the group consisting of calcium, barium, strontium, copper, zinc, magnesium, manganese, cobalt, lead, iron, nickel, chromium, thorium, uranium, aluminum, and combinations thereof.

In one or more embodiments, the cation cross-linker comprises barium.

In one or more embodiments, the alginate hydrogel fiber is index-matched with a medium of interest. In one or more embodiments, the predetermined aqueous medium is cell culture medium or an aqueous medium.

In another aspect, an alginate hydrogel paper comprises one or more of the alginate hydrogel fiber(s) as discussed herein, where the alginate hydrogel fibers are combined to form a woven or non-woven matrix.

In one or more embodiments, the alginate hydrogel paper has a plurality of fibers that comprise inter-fiber cross-links and/or a plurality of fibers that comprise intra-fiber cross-links.

In one or more embodiments, the thickness of the alginate hydrogel paper ranges from about 75 μm to about 400 μm. Papers can be prepared with thicknesses that are as thick as 5 mm. These thicker papers work just as well.

In one or more embodiments, the porosity of the alginate hydrogel paper ranges from about 10% to about 60%, and preferably about 20% to about 40% by volume.

In one or more embodiments, the fibers of the alginate hydrogel paper further comprise at least one coating of one or more stabilizing polymers.

In one or more embodiments, the coating comprises alternating layers of positively-charged and negatively-charged polymers.

In one or more embodiments, the coating comprises fibroin.

In one or more embodiments, the paper is used to conduct a chemical, biochemical, diagnostic, cellular, and/or non-cellular analysis.

In another aspect, a three-dimensional cellular array, comprising:
a substrate comprising an alginate hydrogel paper as described herein; and
a medium comprising cells, wherein the cells are positioned within a selected region of the cellular array.

The cells can be localized in a selected region of the array, although the medium may be infused throughout a larger portion of the cellular array and can be infused throughout the entire cellular array. In one or more embodiments, the cellular array has a substrate that comprises a plurality of regions for receiving the carrier fluid and cells.

In one or more embodiments, the selected region comprises hydrogel and cells, and the hydrogel serves to support and contain the cells.

In one or more embodiments, the alginate hydrogel making up the alginate hydrogel paper is substantially index-matched with the medium In another aspect, a three-dimensional cellular array comprises:
a substrate comprising alginate hydrogel paper as described herein, wherein the substrate comprises a plurality of porous regions, each porous region bounded at least in part by a liquid impervious boundary.

In one or more embodiments, the cellular array comprises a plurality of alginate hydrogel papers, and the plurality of the papers are arranged in a stack, or as a cascade or as a loose web or loose net of fibers.

In one or more embodiments, the cellular array further include conventional paper, and for example, the conventional paper is interposed between two alginate hydrogel papers.

In one or more embodiments, the alginate hydrogel paper stack is disposed between a support framework.

In one or more embodiments, the cellular array further comprises cell culture medium comprising cells disposed in the porous region.

In one or more embodiments, the liquid impervious boundary comprises siloxanes, e.g., PDMS, poly(lactic-co-glycolic acid), epoxy, polystyrene, a polyether, a polyamide, acrylates, e.g., PMMA, polycarbonate, polyethylene, polypropylene, a photoresist precursor, a wax, or a fat.

In one or more embodiments, within the cellular array, the alginate hydrogel making up the alginate hydrogel paper is substantially index-matched with a predetermined aqueous medium.

In one or more embodiments, within the cellular array, the difference in refractive indices between the alginate hydrogel paper and the aqueous medium ranges from about 0.01 to about 0.

In one or more embodiments, within the cellular array, the alginate hydrogel has an alginate content in the range of about 0.1% to about 8% by weight of the fiber.

In one or more embodiments, within the cellular array, the cation cross-linker includes barium.

In one or more embodiments, within the cellular array, the medium comprises a biologically derived medium, nutrient medium, and/or simulated bodily fluid.

In one or more embodiments, the alginate hydrogel fiber within the cellular array is used to conduct a chemical, biochemical, diagnostic, cellular, and/or non-cellular analysis.

In another aspect, a method for making alginate hydrogel fiber comprises:
  introducing an aqueous alginate solution into a solution of a water-soluble salt of a cation cross-linker to form an entangled alginate hydrogel fiber; and incubating the entangled fiber in the alginate solution to cross-link the alginate.

In one or more embodiments, the alginate fiber is stirred or is quiescent (e.g., is not stirred) during incubation.

In one or more embodiments, the entangled fiber is incubated in the alginate solution at a predetermined temperature. In another embodiment, the one or more predetermined temperatures ranges from about 20° C. to about 40° C., e.g., from about room temperature to about 37° C.

In one or more embodiments, the alginate comprises barium alginate and the cation cross-linker comprises barium.

In one or more embodiments, the alginate is in an amount of about 0.1% to about 8% by weight of the solution.

In another aspect, a method for index-matching alginate hydrogel paper with aqueous medium comprises:
  determining a refractive index of an aqueous medium of interest;
  preparing alginate solutions with different concentrations of a cation cross-linker and alginate;
  measuring the refractive indices of the alginate solutions; and
  identifying the alginate solution with a refractive index that matches that of the aqueous medium.

In one or more embodiments, the cation cross-linker comprises barium.

In one or more embodiments, the aqueous medium comprises cell culture medium.

In another aspect, a kit for conducting biochemical, diagnostic, cellular, and/or non-cellular analysis comprises alginate hydrogel paper index-matched to aqueous medium. In another aspect, a kit for conducting cellular analysis comprises alginate hydrogel paper index-matched to cell culture medium.

In another aspect, the index-matched alginate hydrogel paper allows visualization of the cellular array using a device that transmits light at different wavelengths. In one or more embodiments, the device is a fluorescent microscope or a light microscope.

Alginate hydrogel fibers can be used in a broad spectrum of biological and medical applications. Alginate hydrogel fibers can be used as a substrate for a variety of biochemical, diagnostic, non-cellular, and cellular assays and analyses, including but not limited to paper-based fluidics, paper-based biochemical or chemical reactions, cell-based assay analysis, and cell culturing. Alginate hydrogel fibers can be used in real-time imaging in three-dimensional cellular bioassays, as well as in the optimization of other techniques such as paper-based transmittance colorimetric assays. Alginate hydrogel fibers are useful in the manufacture of paper and textiles, such as non-woven, porous papers, which also find use in biological and medical applications. The fibers can be used in different types of medical products, including sutures and wound dressing materials. The fibers can be useful for tissue engineering. Alginate hydrogel fibers can be used for waterproofing fabrics and as an impression-making material in dentistry, prosthetics, and life-casting, which is the process of creating a three-dimensional copy of a body.

These and other aspects and embodiments of the disclosure are illustrated and described below.

BRIEF DESCRIPTION OF THE DRAWINGS

The foregoing and other objects of the present invention, the various features thereof, as well as the invention itself, may be more fully understood from the following description, when read together with the accompanying drawings. The drawings are presented for the purpose of illustration only and are not intended to limit the invention.

DETAILED DESCRIPTION

Figure 1:
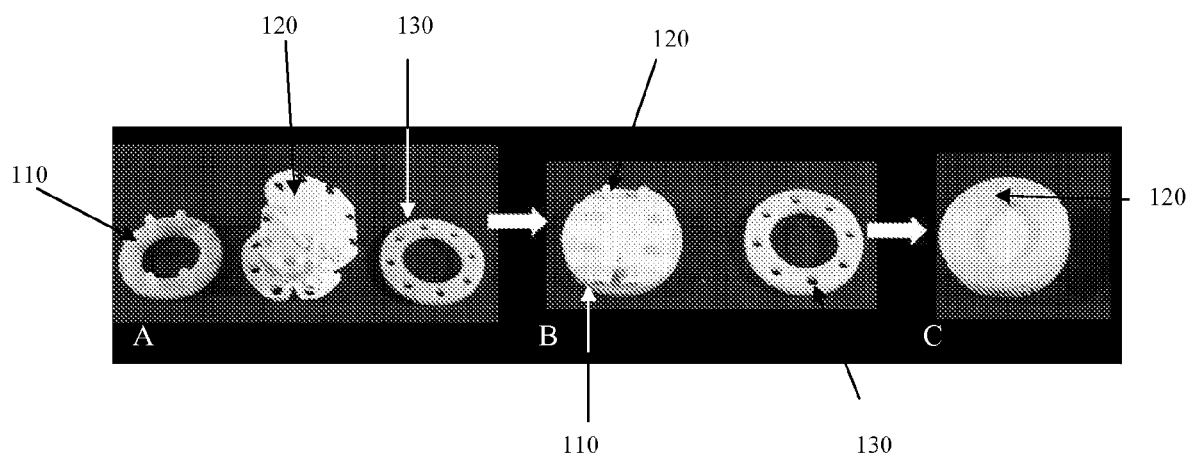
FIG. 1A is an image of a support framework for paper before assembly, with the base 110 of the support framework on the left, stacks of paper in the middle, and the top of the support framework on the right of the image.
FIG. 1B is an image of paper stacks added to the base of the support framework.
FIG. 1C is an image of paper stacks sandwiched between the assembled support framework.

The subject matter discloses alginate hydrogel fibers, papers, and arrays and methods for preparing and using such materials.

Alginate Hydrogel Fiber

In one aspect, the disclosed subject matter provides an alginate hydrogel fiber. The alginate hydrogel fiber is composed of water and a cross-linked alginate, with a low solids content. The low solids content and relatively high water content makes the alginate hydrogel fiber transparent and therefore useful as a medium for objects that can be visualized using light.

Alginate is a biodegradable polymer derived from seaweed. Alginate can be obtained from, for example, green algae (Chlorophyta), brown algae (Phaeophyta), and red algae (Rhodophyta). Alginate is a linear polysaccharide copolymer with two sterically different repeating units, (1→4)-α-L-guluronate (G unit) and (1→4)-β-D-mannuronate (M unit) in varying proportions. Alginate useful in the disclosed fibers has a mannuronic acid to guluronic acid (MG) ratio of about 10% to about 90%, although other variations in composition are contemplated. In some embodiments, alginate useful in making the disclosed fibers has a MG ratio of about 50% to about 70%. Alginate useful in the disclosed fibers has a molecular weight of from about 10 kDa to about 1000 kDa, although other molecular weights are contemplated. In some embodiments, alginate useful in the disclosed fibers has a molecular weight of from about 50 kDa to about 500 kDa. In some embodiments, alginate useful in the disclosed fibers has a molecular weight of from about 100 kDa to about 300 kDa. In some embodiments, alginate useful in the disclosed fibers has a molecular weight of about 240 kDa. Alginate useful in making the disclosed fibers has a viscosity of from about 50 cP to about 600 cP (2% aqueous solution at 25° C.). In some embodiments, alginate useful in making the disclosed fibers has a viscosity of from about 200 cP to about 400 cP (2% aqueous solution at 25° C.).

A "hydrogel," as used herein, is a polymer cross-linked via covalent, ionic, or hydrogen bonds to provide a three-dimensional open-lattice structure that entraps water molecules to form a gel. Alginate polymers can be readily cross-linked by reacting the polymer's carboxylic acid groups with divalent or multivalent cations.

In one or more embodiments, an alginate hydrogel fiber is composed of water in an amount of more than about 92% by weight of the fiber, e.g., about 92-99.9% by weight, or about 94%, 95%, 96%, 97%, 98%, 99% or 99.5% by weight, and a cross-linked alginate in an amount of about 0.1% to about 8% by weight of the fiber, e.g., about 6%, 5%, 4%, 3%, 2%, 1% or 0.5% by weight. In another embodiment, an alginate hydrogel fiber is composed of a cross-linked alginate in an amount of about 2% by weight of the fiber. In another embodiment, an alginate hydrogel fiber is composed of a cross-linked alginate in an amount of about 0.5% by weight of the fiber. In another embodiment, the alginate hydrogel fiber includes additional additives. Various additives are contemplated, including but are not limited to one or more salts, amino acids, peptides, polypeptides, organic molecules, drugs, signaling molecules, antibiotics, vitamins, etc Alginate fibers can be prepared by introducing an aqueous alginate solution into a solution of a water-soluble salt of a cation cross-linker. The cation salt solution can be stirred or can remain quiescent (e.g., not stirred). In an alternative arrangement, the stirred or quiescent cation salt solution can be added to the alginate solution. The alginate is introduced from a reservoir through a nozzle, syringe, or other applicator. The applicator diameter and fluid flow rates can be varied to vary the fiber thickness. Suitable modifications to this technique will be readily apparent to those of skill in the art; these modifications are all contemplated for use with this invention.

In one or more embodiments, the alginate hydrogel fiber has a diameter of about 0.1 mm to about 1 mm. In one embodiment, the fiber has a diameter of about 0.1 mm to about 0.5 mm. In another embodiment, the fiber has a diameter of about 0.1 mm.

The alginate in the alginate hydrogel fiber is cross-linked to enhance its structural integrity. In one or more embodiments, the alginate is cross-linked with a divalent or multivalent cation. Suitable cation cross-linkers include, but are not limited to multivalent cations such as calcium, barium, strontium, copper, zinc, magnesium, manganese, cobalt, lead, iron, nickel, chromium, thorium, uranium, and aluminum, either alone or in combination with any of the above named cations. In one or more embodiments, the cation cross-linker is barium, either alone or in combination with any of the above named cations. The cation crosslinker can be calcium or barium or strontium or copper or zinc or magnesium or manganese or cobalt or lead or iron or nickel or chromium or thorium or uranium or aluminum.

The alginate fiber can be of any length. For example, the length of the alginate hydrogel fiber can range from the order of centimeters to kilometers. In one embodiment, the fiber is a continuous strand with a length of about 5 m to about 15 m. In one or more embodiments, the fiber is a continuous strand with a length of about 10 m. Other fiber lengths can be obtained. For example, shorter fiber lengths could be obtained by more vigorous (or shear) stirring of the fiber-forming solution. In other embodiments, to provide different fiber lengths, the introduction of alginate solution into the cross-link solution can be continuous or intermittent. Many variations of the fiber length are contemplated, as the fibers can be cut or synthesized into any pre-determined fiber length.

In one or more embodiments, the fiber is used to conduct a chemical, biochemical, diagnostic, cellular, and/or non-cellular analysis Alginate Hydrogel Paper The alginate fibers (coated or uncoated) can be used to prepare paper, e.g., non-woven mats. An alginate hydrogel paper includes one or more alginate hydrogel fibers, which form a non-woven matrix. The alginate hydrogel paper includes intra-fiber cross-links and also inter-fiber cross-links when multiple fibers are used. Cross-links increase the strength and structural integrity of the resultant paper.

Hydrogel alginate paper is prepared by introducing an aqueous solution of a soluble alginate, such as sodium alginate, into a stirred or quiescent solution of a water-soluble salt of a cation cross-linker and allowing the fibers to become entangled into a non-woven mesh. The alginate is introduced from a reservoir through a nozzle, syringe, or other applicator. The concentration of alginate and cross-linker in the respective solutions can be selected to obtain a hydrogel fiber of desired alginate content. In one embodiment, the method for making alginate hydrogel fiber includes:

introducing the aqueous alginate solution into the stirred solution of the water-soluble salt of a cation, such that an alginate hydrogel fiber(s) is formed; and incubating the fibers in the alginate solution without stirring to entangle the fibers and ensure stable cross-linking of the alginate.

In some embodiments, the solution of the water-soluble salt is stirred. Stirring can further entangle the alginate hydrogel fibers. In other embodiments, the solution of the water-soluble salt is quiescent. In some embodiments, the entangled fibers in the alginate solution are incubated at one or more pre-determined temperatures. In some embodiments, the incubation temperature ranges from about room temperature (e.g., ca. 20° C.) to about 37° C. The degree of entanglement or weave can be varied from a tight dense mesh or matrix to a loose net or web.

In other embodiments, the fibers are collected and woven to form a woven matrix.

In one or more embodiments, the method includes using alginate solution, wherein the alginate is in an amount of about 0.1% to about 8% by weight of the solution. In one or more embodiments, the method for making alginate hydrogel fiber includes using sodium alginate solution as the precursor alginate solution and barium cation cross-linker. The aqueous medium is typically water, but can also be a buffer or culture medium, such as a cell culture medium. Using these solutions instead of just water may change the final refractive index of the fiber, which provides greater flexibility in fiber matching. The aqueous medium can also include organic solvents.

There could be advantages here (for example, if one wanted to impregnate the fibers with cells or proteins). Suitable concentrations of the water-soluble cation salt, e.g. divalent or multivalent cation salt solution, ranges from about 0.001 M to about 2 M. Incubation time is a function, among other factors, of alginate and crosslinker concentrations. For example, lower cation crosslinker concentrations require longer incubation times for cross-linking. In one or more embodiments, suitable concentrations of the water-soluble cation salt solution ranges from about 0.05 to about 0.5 M. Incubation can be performed for a time sufficient to allow the cation cross-linker to diffuse through the entire thickness of the hydrogel fiber, thus ensuring fiber stability. In certain embodiments, incubation times ranging from about 1 minute to about 5 minutes at temperatures ranging from 20-40° have been found sufficient.

The concentration of alginate and cross-linker in the respective solutions can be varied to provide an alginate fiber of predetermined properties, such as water content, cross-link density, mechanical wet strength, or refractive index. For example, the alginate concentration can be selected to provide a solution that best matches the refractive index of a culture medium intended for use with the alginate fiber, as described in more detail herein. The concentration of the cation cross-linker, which is a factor in the kinetics of gelation, also affects fiber thickness and porosity. In one or more embodiments, different cations can be added to the hydrogel, which affects fiber thickness and porosity. In this way, it is possible to obtain fibers of different thickness and porosity using the same solids content of precursor alginate The fiber can be removed from bath solutions by using instruments such as tweezers, screens or automatic dipping instruments known in the art. Paper is formed into desired final form using techniques common to the papermaking art, such as, for example, screens and fabrics for laying up fibers, presses to remove excess water, and calendars to obtain a final thickness and smoothness. Care can be taken to reduce undesired water loss due to evaporation, by, for example, being expeditious during any process that requires handling the paper outside of an aqueous medium and/or storing or protecting the paper in protective water-impermeable sheets. In one or more embodiments, the paper is compressed to further stabilize the fibers. Compression also serves to remove excess water.

The cross-links result in paper with a three dimensional structure that can be used as a support in diagnostic devices and cellular assays. For example, the paper can have a porosity dimension ranging from about 5 µm to about 100 µm. In one or more embodiments, the porosity dimension ranges from about 10 µm to about 50 µm. Porosity can be controlled by, for example, fiber content of the paper, the initial fiber diameter and by compressing the fibers during the paper making step. In one or more embodiments, the porosity is 3-dimensional and is defined by pore volume; pore volume and pore size can be selected to provide interstitial spaces suitable for cell attachment and proliferation.

The inter-fiber distance, and thus, porosity, of the paper helps define its thickness. Increasing the inter-fiber distance increases paper thickness. Other factors that define paper thickness include the initial fiber diameter, the volume of cross-linked alginate used (which affects fiber length), and the settings of the compression or calendaring machine that compresses fibers into paper. For example, increasing the gap distance of the compression or calendaring machine results in thicker fibers. In one or more embodiments, the paper ranges in thickness from about 75 µm to about 400 µm. In one or more embodiments, the paper ranges in thickness from about 150 µm to about 300 µm. In one or more embodiments, the paper has a thickness of about 250 µm. In one or more embodiments, the paper has a porosity, i.e., pore volume that ranges from about 10% to about 60%, or to about 20% to about 40% by volume of the alginate hydrogel paper. In one or more embodiments, the paper has a porosity of about 30% by volume. Papers as thick as thick as 5 mm can be prepared. These thicker papers work just as well.

The alginate hydrogel paper can include other additives and coatings, such as a protective coating over the fibers, which can be applied before, during or after the paper forming step. Alginate hydrogel fibers where the liquid content can be susceptible to swelling, in particular when the alginate hydrogel fibers are water-based when placed in cell culture medium. Because cell culture medium can contain many ions, small molecule metabolites, and fetal bovine serum (for example, 10%), placement of the fibers (which may be free of such electrolytes and small molecules) in the cell culture medium can induce swelling. This swelling destabilizes the paper; fiber-fiber contacts are lost, and the paper disassociates into a collection of loose fibers. To improve the stability of the alginate hydrogel fibers (for example, by protecting them from the surrounding cell culture medium), the alginate hydrogel paper can be coated with a stabilizing polymer. Additives and coatings to the alginate hydrogel paper include, but are not limited to: proteins such as fibroin, natural polysaccharides such as alginate and chitosan, cationic and anionic polymers and branched and linear polymers such as polyethyleneimines and poly(dimethyldiallylammonium chloride), respectively. In one or more embodiments, alginate is used both for the fiber and the coating. As alginate is a negatively charged polymer, it can be applied as a component of a by-layer coatings to the crosslinked fiber.

In certain embodiments, the stability of the final paper is improved by coating the paper after pressing, and the raw fiber goes unprocessed. Thus, there are at least two ways to stabilize the paper using coatings: (i) hydrogel fiber is treated, then pressed into paper or (ii) the hydrogel fiber is pressed into paper, then the paper is treated. In one or more embodiments, both methods of making and stabilizing alginate paper; e.g., fiber→coated fiber→paper
fiber→paper→coated paper results in the fibers themselves being coated, whether or not they are in "paper" form.

Coating before or after paper formation, and/or before or after fiber compression will increase cross-link stability.

These coatings are selected as not to significantly affect the index of refraction such that the paper remains transparent when visualized, such as through the use of light or fluorescent microscopy. The stability of the fiber is related to the number of coatings. For example, uncoated fibers are stable for a set time period, such as several hours, allowing the paper to be used to culture and release cells. Single coatings may increase the length of time that the paper is stable, allowing for, e.g., days of stability. Multiple coatings allow use of the paper in the range of days to weeks. Stability of the fiber is also affected by the polymer concentration or molecular weight of the alginate.

In one or more embodiments, the fibers are coated with alternating layers of positively-charged and negatively-charged polymers. The coatings are obtained by dipping the entangled alginate hydrogel fiber into a polymer solution for a defined period of time, removing the entangled fibers, lightly blotting away excess liquid, and placing the fibers into the next solution. In other embodiments, one can also coat single fibers as they are extruded in a continuous fashion, i.e. passing fibers from bath to bath on spools, as used in industrial applications. This process is repeated multiple times, e.g., 2-12 times to create 1-6 layers, where each layer contains both a positively-charged and negatively-charged polymer. Other methods of coating fibers using known coating methods can be readily adapted for the coating of the alginate hydrogel fibers described herein.

In one or more embodiments, the fibers are coated with a stabilizing polymer comprised of fibroin. Fibroin is a protein created for example by silkworms (*Bombyx mori*) or spiders in producing silk. Fibroin is an essential component of raw silk and spider-web filaments. Fibroin consists of layers of anti-parallel beta sheets, which give fibroin its tensile strength. The paper is coated with a dilute solution of fibroin, ranging from 0.05% to 5% (w/v). The coating is prepared by submerging the paper into the fibroin solution for a defined period of time and then submerging the paper with ethanol for a defined period of time. Dipping in ethanol sterilizes the paper and cross-links the fibroin, increasing paper strength. This step can be repeated depending on the number of coatings desired.

In another aspect of the disclosure, alginate hydrogel fiber or paper can be index-matched to a culture medium or other aqueous medium that is used in testing or assaying. Culture medium is a liquid or gel designed to support the growth of microorganisms or cells. Cell culture medium includes buffered aqueous solution, including nutrient rich solutions and other additives useful to support cell or microorganism growth. Culture media can vary in pH, glucose concentration, growth factors, and the presence of other nutrients. The growth factors used to supplement media can be derived from animal fluids, such as calf serum. Any medium typically used in cell culturing, cell assay and other biological and biochemical diagnostics can be used and index-matched, if desired. For example, nutrient broths, nutrient broth derivatives (including serum and/or antibiotics), and simulated bodily fluids can be used as the culture media. The alginate paper may also be indexed matched to other fluids, e.g., biologically-derived fluids that may be used in a bioassay, screening or diagnostic assays. By way of example, the fluid can be blood, plasma, urine, sputum, interstitial fluids, or other bodily fluid. Culture medium can be used as the liquid medium in a hydrogel. Alternatively, water itself without any additives can be used as the liquid medium in a hydrogel.

Alginate hydrogel paper that is index-matched, e.g., to culture medium, allows the paper to appear transparent, which facilitates the use of microscopy to image cells and biological materials within a single layer or multiple stacks of alginate hydrogel paper. Visualization of the alginate hydrogel paper through microscopy can be performed using any device capable of transmitting light at different wavelengths. For example, the device is a fluorescent or light microscope.

In certain embodiments, the cationic cross-linker of the index-matched alginate paper is barium. In certain embodiments, the alginate hydrogel fiber has an alginate content of about 0.1% to about 8% by weight. In other embodiments, the alginate hydrogel fiber has an alginate content of about 0.5% to about 2% by weight. As is discussed in more detail below, it has been surprisingly found that barium alginate provide particularly good index matching with culture medium. Such alginate fibers can be index-matched with a range of media.

Three-Dimensional Cellular Array

In certain instances, the present disclosure provides three-dimensional cellular arrays prepared using alginate hydrogel paper that are capable of growing and maintaining cells. A three-dimensional cellular array includes alginate hydrogel paper sheets that are used as a single layer or that can be arranged in a stack. The multi-layer array forms a tissue-like construct. The three-dimensional cellular array not only more accurately mimics tissues but also facilitates an environment to assay the effects of metabolite and nutrient gradients on cell growth and mobility.

Figure 4:
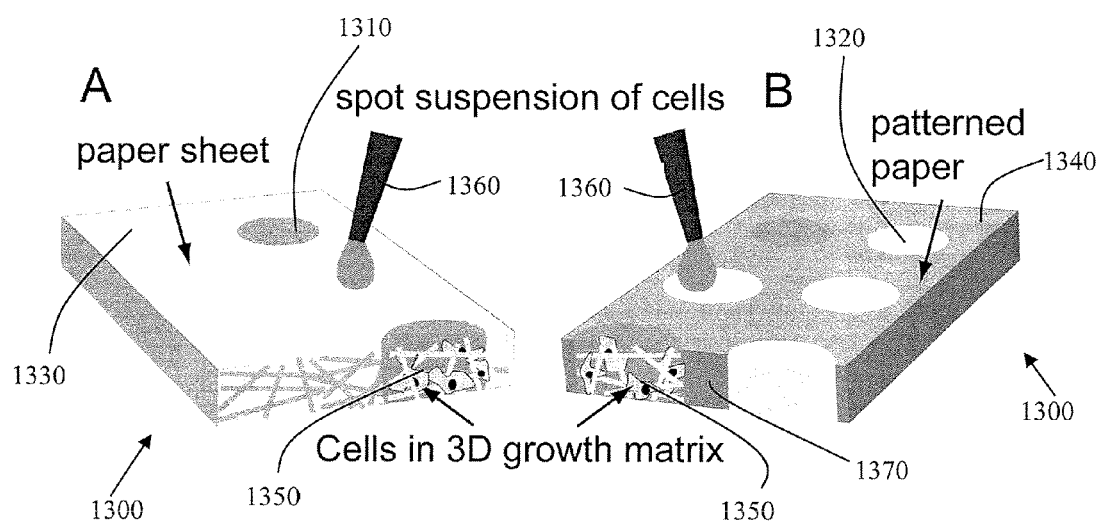
FIGS. 4A and 4B are schematic illustrations of a cellular array (A) prepared from alginate paper and (B) prepared from alginate paper having hydrophobic liquid impermeable and hydrophilic porous regions.

As described with reference to FIG. 4A, the cellular array 1300 can be made by contacting, e.g., spotting, the alginate paper substrate 1300 with a suspension of cells in a hydrogel or hydrogel precursor, culture medium or the like using an applicator 1360. As the substrate is porous and hydrophilic, the dimensions of the wells 1310 are dictated by the thickness of the alginate paper as well as the distance the suspension of cells wicks or spreads laterally through the substrate 1330 (see FIG. 4A). Because liquids and gels yield spots of defined lateral dimensions when spotted onto paper or other porous hydrophilic substrates, three-dimensional cell cultures of desired lateral dimensions can be obtained by spotting defined volumes of a suspension of cells in an appropriate carrier onto the porous alginate hydrogel paper substrate. The lateral dimensions of the spot (i.e., the lateral size of the three-dimensional culture) can be controlled by controlling the volume of the spotted liquid. Vertical dimensions (thickness) of the three-dimensional culture are defined by the thickness of the alginate hydrogel paper. Repetition of the spotting process yields patterned three-dimensional cultures on a single piece of paper (i.e., arrays of cells). The spotting can be performed such that the resulting patterns can be readily recognized by an existing cell culture and screening interface (e.g., 384-well layout can be generated by spotting a 16×24 array of spots with 4.5 mm vertical and horizontal pitch).

In some instances, the three-dimensional cellular arrays are made using patterned substrates, e.g., patterned alginate hydrogel paper. Because liquids and gels can readily wick into alginate substrates, patterning the paper with liquid impermeable (hydrophobic) borders can be used to dictate not only the physical dimensions but also the shape of the cell growth substrate. Accordingly, in some embodiments, the substrate is patterned into hydrophobic and hydrophilic regions. When the substrate is patterned, e.g., contains hydrophilic and hydrophobic areas, as is illustrated by substrate 1340 in FIG. 4B, the dimensions of the wells 1320 are dictated by the thickness of the substrate and the size of the hydrophilic areas of the alginate hydrogel paper substrate. In such embodiments, the hydrophilic regions are bounded by hydrophobic barriers or walls 1370, which limit the lateral flow of the suspension of cells.

In one or more embodiments, the three-dimensional cellular array includes areas, or "wells," which contain cells within a three-dimensional alginate hydrogel paper that are bounded by a fluid impervious boundary. In one or more embodiments, the liquid impervious boundary is, for example, PDMS, poly (lactic-co-glycolic acid), epoxy, polystyrene, a polyether, a polyamide, PMMA, polycarbonate, polyethylene, polypropylene, a photoresist precursor, a wax or a fat.

Any method of patterning the hydrophilic substrate can be used. By way of example, the hydrophobic layer can be applied directly to the porous substrate to produce patterned regions having hydrophilic or hydrophobic properties using printing, such as from an ink jet printer, liquid transfer, such as in stamping or other printing methods, or silk screening. The hydrophobic pattern can also be made using photolithography, in which the paper is infused with photoresist and then exposed to light to produce regions of hydrophobic photoresist and regions of hydrophilic resist-free paper. Exemplary methods are known in the art and described in, e.g., International Publication No. WO 2008/049083, entitled "Lateral Flow and Flow-Through Bioassay Based on Patterned Porous Media, Methods of Making Same, and Methods of Using Same," filed on Oct. 18, 2007, which is incorporated in its entirety by reference. Further details on the patterned cellular array are found in International Publication No. WO 2009/1200963, entitled "Paper-Based Cellular Arrays," filed on Mar. 27, 2009, the contents of which are hereby incorporated in its entirety herein.

The cells can be spotted using any cell-compatible carrier. In certain embodiments, the carrier is a culture medium as discussed herein.

In certain embodiments, the carrier is a hydrogel that can be applied in a low viscosity state to the alginate paper cell plate and thereafter converted into a high viscosity gel once applied. Any known hydrogel or hydrogel precursor can be used for the cell-containing hydrogel. For example, methods of forming hydrogels using paper are described in International Publication No. WO 2009/121038, entitled "Shaped Films of Hydrogels Fabricated Using Templates of Patterned Paper," filed Mar. 27, 2009, incorporated in its entirety by reference. In one exemplary method, an ionotropic hydrogel is formed by contacting the substrate with a solution of one or more gelling agents, including but not limited to metallic ions, such as $Pb^{2+}$, $Ba^{2+}$, $Fe^{3+}$, $Al^{3+}$, $Cu^{2+}$, $Cd^{2+}$, $Ho^{3+}$, $Ca^{2+}$, $Zn^{2+}$, $Co^{2+}$, $Ni^{2+}$, $Mn^{2+}$, and $Mg^{2+}$, and contacting the substrate with a hydrogel precursor, including but not limited to alginic acid (AA), carboxymethylcellulose (CMC), i-carrageenan, poly(galacturonic acid) (PG), poly(bis(4-carboxyphenoxy)-phosphazene, PURAMATRIX™, and thermal responsive hydrogels such as MATRIGEL™. The interaction of the gelling agent, e.g., ion, with the hydrogel precursor results in the gelation of the hydrogel. As discussed herein, a protective coating or liquid impermeable barrier can prevent the paper fibers from destabilizing.

After contacting the substrate of the cellular array with a suspension of cells in a hydrogel or hydrogel precursor, the substrate is maintained under suitable conditions that allow gelation of the hydrogel within the alginate hydrogel paper substrate. As described herein, suitable conditions include maintaining the substrate at a particular temperature or contacting the substrate with a gelling agent.

The resulting three-dimensional cellular array is stable and can be maintained in conditions suitable for cell growth. Such culture conditions are known in the art (see, e.g., Culture of Animal Cells: A Manual of Basic Techniques, Freshney, R. I. ed., (Alan R. Liss & Co., New York 1987); Animal Cell Culture: A Practical Approach, Freshney, R. I. ed., (IRL Press, Oxford, England 1986)). For example, the cellular array can be immersed in cell culture medium suitable for a particular cell type and maintained in an incubator.

The array can have different shapes, sizes, and paper sheets. The number of paper sheets ranges from about 1 sheet to about 50 sheets. In one or more embodiments, the number of paper sheets ranges from about 5 sheets to about 10 sheets. The number of paper sheets helps dictate the thickness of the array. In one or more embodiments, the array has a thickness of about 75 μm to about 3.5 mm. In one or more embodiments, the array has a thickness of about 200 μm to about 2 mm. In one or more embodiments, the array has a thickness of about 400 μm to about 1 mm.

The array can include one or more materials other than alginate hydrogel papers. For example, it can have one or more non-alginate layers, such as conventional paper, e.g., cellulosic paper, is interposed between the alginate hydrogel layers. By way of example, the alginate hydrogel paper layers in the three-dimensional cellular array are disposed between and supported by a support framework. In one or more embodiments, the support framework is made of plastic. In one or more embodiments, the plastic support framework is in the shape of a disc with holes for securing the papers, as illustrated in FIGS. 1A-1C. FIG. 1A is an image of a support framework before assembly, with the base 110 of the support framework on the left, paper stacks 120 in the middle, and the top 130 of the support framework on the right of the image. FIG. 1B is an image of paper stacks added to the base of the support framework. FIG. 1C is an image of paper stacks sandwiched between the assembled support framework. The support framework provides rigidity and support to the three-dimensional cellular array. The papers can also be stacked in other arrangements, such as in a cascade of papers, with one paper offset from another.

In one or more embodiments, a three-dimensional cellular array comprises:
 a substrate comprising alginate hydrogel paper as described herein; and
 a medium comprising cells, wherein the cells are positioned within a selected region of the cellular array.

In one or more embodiments, the selected region comprises hydrogel and cells, and the hydrogel serves to support and contain the cells.

In another aspect, a three-dimensional cellular array comprises:
 a substrate comprising alginate hydrogel paper as described herein, wherein the substrate comprises a plurality of porous regions, each porous region bounded at least in part by a liquid impervious boundary.

In one or more embodiments, the cellular array comprises a plurality of alginate hydrogel papers, and the plurality of the papers are arranged in a stack.

In one or more embodiments, one or more sheets of alginate paper containing cell-free hydrogels can be overlaid with one or more alginate hydrogel paper sheets with cell-containing hydrogels to arrive at a multi-layer array. In one or more embodiments, one or more of the layers can contain an agent, for example, a chemical agent or a chemoattractant. For example, a number of hydrogel-containing sheets can be stacked on top of a chemoattractant-containing layer, and a cell-containing layer can be placed on top of the stack.

A three-dimensional cellular array described herein can be loaded with cells simultaneously with a cation solution and/or hydrogel polymer. In some embodiments, the array is loaded with cells after the cation solution and/or hydrogel polymer is contacted with the alginate hydrogel paper.

Cells that can be grown in the arrays can be any prokaryotic or eukaryotic cell. Such cells include, for example, bacterial cells (such as *E. coli*), insect cells, yeast cells, or mammalian cells (such as Chinese hamster ovary cells (CHO) cells, COS cells, VERO cells, BHK cells, HeLa cells, Cv1 cells, MDCK cells, 293 cells, 3T3 cells, or PC12 cells). Other exemplary cells include cells from the members of the genus *Escherichia, Bacillus, Lactobacillus, Rhodococcus, Pseudomonas, Aspergillus, Trichoderma, Neurospora, Fusarium, Humicola, Rhizomucor, Kluyveromyces, Pichia, Mucor, Myceliophtora, Penicillium, Phanerochaete, Pleurotus, Trametes, Chrysosporium, Saccharomyces, Schizosaccharomyces, Yarrowia*, or *Streptomyces*. Other cells include CD90+/CD45− hepatic tumor stem cells. In certain instances, the cells can be transformed or transfected with one or more expression vectors or viral vectors.

After cell culture, the layers of the array can be de-stacked for analysis using biochemical techniques known in the art. For instance, the array can enable real-time imaging in three-dimensional cellular bioassays and assist in optimizing paper-based transmittance colorimetric assays. Any cell-based assay known in the art can be performed using the three-dimensional cellular arrays described herein. For example, the three-dimensional cellular arrays described herein can be used in screening for agents that influence cell function, such as cell viability, apoptosis, proliferation, migration, and gene expression. Test agents can be added to the cellular arrays, can be adsorbed or covalently attached to the hydrogel or substrate (e.g., alginate paper), or can be also included in a biodegradable matrix coated on the substrate (e.g., alginate paper). The cell assay can be designed to investigate whether cells can migrate from cell-rich layers to cell-poorer layers. The stacking of multiple layers of paper permeated with suspension of cells can be used to investigate proliferation of cells in nutrient- and oxygen-limited conditions. Paper arrays that contain cells can be stacked with arrays that contain other cell types to produce a co-culture. Responses of both cell types in this sheet co-culture can be readily investigated after the sheets are disassembled.

In other embodiments, the alginate paper and three-dimensional array can be used in a broad spectrum of biological and medical applications. Alginate hydrogel fibers can be used as a substrate for a variety of biochemical, diagnostic, non-cellular and cellular assays and analyses, including but not limited to paper-based fluidics, paper-based biochemical or chemical reactions, cell-based assay analysis, and cell culturing. Alginate hydrogel fibers can be used in real-time imaging in three-dimensional cellular bioassays, as well as in the optimization of other techniques such as paper-based transmittance colorimetric assays. In one aspect of paper-based diagnostic analysis, the paper is treated with a hydrophobic polymer to create small channels that route fluids through capillary action. Thus, the paper can be used to direct a drop of fluid (e.g., blood, plasma, urine, sputum, interstitial fluids, etc.) through various paths, after which a diagnostic test can be performed on the fluid through interaction with a diagnostic reagent. A diagnostic reagent is a substance that is used in a chemical reaction to detect, analyze or produce another substance which indicates the presence of a special condition. Diagnostic tests may include tests that are, for example, antibody-based, enzymatic, or based on the detection of pH, small molecules, peptides, etc. Such diagnostic reagents have reporter elements that conjugate to the reagents, and thus, the reagents can be used to perform diagnostic assays on the alginate hydrogel paper disclosed herein.

Thus, the alginate fiber, paper, and arrays can be used in paper-based microfluidic systems. In one aspect of paper-based diagnostic analysis, the paper is treated with a hydrophobic polymer to create small channels that route fluids through capillary action. Thus, the paper can be used to direct a drop of fluid (e.g., blood) through various paths, after which a diagnostic test can be performed on the fluid through interaction with a diagnostic reagent. In most embodiments of paper-based microfluidic systems for diagnostics, the readout method is based on color: i.e., the production of an insoluble dye that stays within the pores of the paper and is later visualized. Transparent alginate paper could provide advantages over traditional paper for visualizing the production of these dyes. Further details on paper-based microfluidic systems are found in U.S. Publication No. WO 2011/0111517, entitled "Paper-Based Microfluidic Systems," filed on Mar. 27, 2009, the contents of which are hereby incorporated in its entirety herein.

Index-Matching Alginate Hydrogel Paper with Cell Culture Medium

Paper made from cellulose fibers has been used as a support for three-dimensional cell culture and tissue-based bioassays. However, the optical properties of cellulose fibers impede the use of microscopy as a tool to image live cells within a single layer and multiple stacks of paper because of scatter and the large refractive index contrast between the cellulose fibers and the cell culture medium.

It has been surprisingly discovered that the optical properties of alginate hydrogel paper, unlike those of cellulose paper, allow the alginate hydrogel paper to be index-matched to the aqueous medium and, thus, to reduce scatter of cells and other materials, such as biological materials. In particular, it has been discovered that hydrogel fiber sheets prepared using low solids content alginate, e.g., about 0.1% to about 8% by weight alginate, are well suited for index-matching with aqueous medium, including cell culture medium, simulated bodily fluids, and bodily fluids.

After cell culture, the layers of the three-dimensional cellular array can be de-stacked for analysis using biochemical techniques known in the art. Index-matching can allow the alginate hydrogel paper sheets of the three-dimensional cellular array to appear transparent, which facilitates the imaging of cells, including live cells, within a single layer and multiple stacks of alginate hydrogel paper. More specifically, index-matching allows more light to be collected during visual imaging, resulting in a higher numerical aperture of the optical system and an increased depth of field, which are both important for increasing image resolution through thick materials. Visualization of the alginate hydrogel paper, including cells within the paper, can be performed using any device capable of transmitting light at different wavelengths. For example, the device is a fluorescent or light microscope. Index-matching facilitates live cell imaging within the three-dimensional cellular array, such that the cells can be viewed in a microfluidic device without removing the cells from the array.

In one or more embodiments, the alginate hydrogel paper and aqueous medium have substantially the same index of refraction. In one or more embodiments, the difference in refractive indices between the paper and the aqueous medium ranges from about 0.01 to about 0. The difference in refractive indices can also be manipulated by changing the amount of alginate present in the alginate hydrogel fibers. For example, decreasing the amount of alginate in the alginate hydrogel fiber decreases its refractive index.

In another aspect, the disclosure provides a method for index-matching alginate hydrogel paper with aqueous medium. In one embodiment, the method includes:

identifying the refractive index of the cell culture medium or other aqueous medium of interest;

preparing alginate solutions with different concentrations of a cation cross-linker and alginate; and measuring the refractive indices of the alginate solutions; identifying the alginate solution with a refractive index that matches that of the aqueous medium.

While the refractive index of alginate hydrogel paper is not directly measured, the liquid alginate solutions serve as an accurate indicator of the hydrogel paper optical performance. A Bausch and Lomb Abbe Refractometer can be used to measure the refractive indices of the liquid solutions. The refractive index of cell culture medium is about 1.3335. The refractive index of 0.5% (w/v) sodium alginate is about 1.3335. The refractive index of 2.0% (w/v) sodium alginate is about 1.3345. While not bound by any mechanism of action, the refractive index of the alginate solution likely increases slightly as it changes state from liquid solution to cross-linked alginate gel. Alternatively, the refractive index of alginate hydrogel paper can be qualitatively determined by submerging the paper into solutions of known refractive indices and comparing the resolution of patterns on the paper that are imaged using light, including but not limited to the use of microscopy, such as fluorescent or light microscopy. Thus, paper with patterns of high resolution has a refractive index that is substantially the same as the solution with a known refractive index.

Alginate hydrogel fibers can have different cation cross-linkers that result in alginate hydrogel papers with different optical properties. This will allow a range of culture medium to be used having a range of indices, while still maintaining an index of refraction match. The cation cross-linker comprises calcium, barium, strontium, copper, zinc, magnesium, manganese, cobalt, lead, iron, nickel, chromium, and aluminum ions. In selecting an appropriate alginate paper for use in cell culture, factors such as the optical properties of the paper and cell compatibility are considered. Use of barium as the cationic cross-linker has been found to be especially useful in index-matching with culture medium, including but not limited to RPMI, DMEM, HBSS, LB, and other variants. Culture media can vary in pH, glucose concentration, growth factors, and the presence of other nutrients. Any medium typically used in cell culturing, cell assay and other biological diagnostics can be used and index-matched, if desired. For example, nutrient broths, nutrient broth derivatives (including serum and/or antibiotics), and simulated bodily fluids can be used as the culture media. The alginate paper may also be indexed matched to other fluids, e.g., biologically-derived fluids that may be used in a bioassay, screening or diagnostic assays. By way of example, the fluid can be blood, plasma, urine, sputum, interstitial fluids, or any other bodily fluids. Simulated bodily fluids can also be used as the culture media.

In one aspect, barium cation cross-links alginate such that the resulting barium alginate does not scatter light. The low light scattering effect of barium cation cross-linker provides exceptional imaging capability of a cell culture entrained within the hydrogel paper. In addition, barium exhibits low cell toxicity for a range of cells. Barium alginates have been implanted in animal models with no demonstrable toxicity. This low cell toxicity is due to the barium cation's high affinity for alginic acid and to numerous washing steps to remove excess barium cation. In contrast to barium, while many divalent transition metals, e.g., Co, Ni, Cu, Pb, Cr, can be successfully used to prepare hydrogels with a range of refractive indices or light scattering, these cations can be cytotoxic under some conditions.

In another aspect, the disclosure provides a kit for conducting a biochemical, diagnostic, cellular, and/or non-cellular analysis, comprising alginate hydrogel paper index-matched to aqueous medium. In another embodiment, the kit is for conducting cellular analysis, comprising alginate hydrogel paper index-matched to cell culture medium.

The following examples are provided to illustrate, not limit, the invention.

EXAMPLES

Example 1

The Preparation of Alginate Hydrogel Fiber and Paper

In this example, the preparation of a representative alginate hydrogel fiber, barium alginate hydrogel fiber, and barium alginate paper is described.

Barium alginate hydrogel fiber was fabricated by preparing a 0.5% (w/v) solution of sodium alginate (Ca. 240 kDa) in MilliQ water. Next, 3 mL aliquots of sodium alginate were manually introduced into a rapidly stirred solution of 0.5 M barium chloride using a syringe and 21-gauge needle. Alginate hydrogel fiber formed instantaneously, and the stirring created an entanglement of the fiber. The entangled fiber was incubated for an additional 3 minutes in the barium solution at room temperature without stirring to ensure stable cross-linking of the alginate.

Barium alginate paper was prepared by compressing the fiber to further interweave the fiber and create a single sheet of barium alginate paper. The distance between the rollers of the pasta machine helped control paper thickness. The paper was cut into 2 cm×2 cm squares and autoclaved for cell culture experiments. FIGS. 2C-2F and 3A-B depict barium alginate paper, and FIGS. 2A-B depict Whatman 414 Filter Paper used as a control.

Barium alginate hydrogel fibers have optical properties that allow it to be index-matched to, for example, cell culture medium. Barium alginate paper that was index-matched to cell culture medium facilitated live cell imaging using microscopy.

Figure 2:
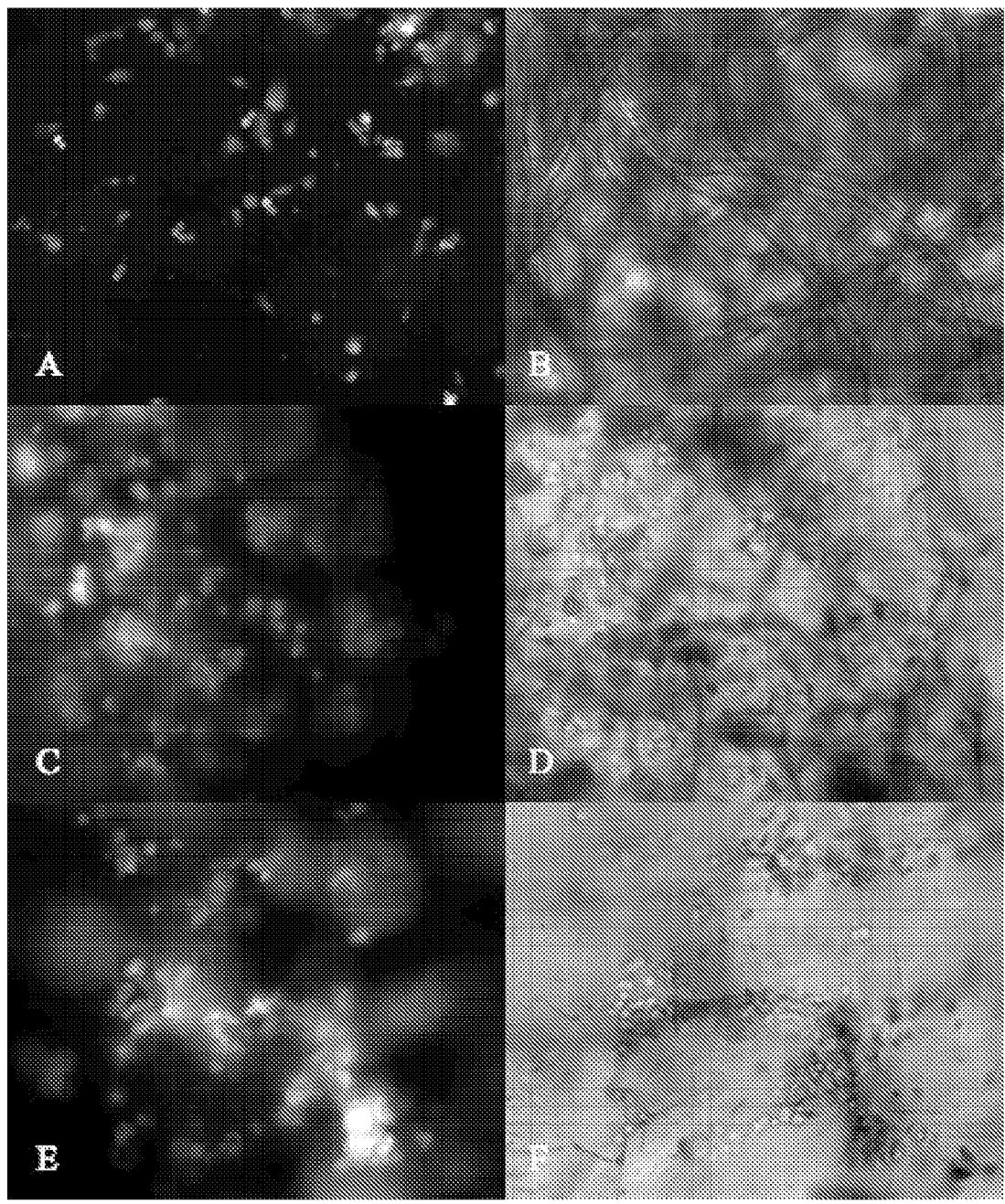
FIGS. 2A-2B are fluorescence microscopy images of a single layer of Whatman 414 Filter Paper after culturing with green fluorescent protein-expressing human breast adenocarcinoma (GFP-MDA-MB-231) cells for 18 hours (A) magnified 10× by fluorescence (1000 ms exposure) and (B) under brightfield (1 ms exposure), respectively.
FIGS. 2C and 2D are images of 0.5% (w/v) barium alginate paper after culturing with green fluorescent protein-expressing human breast adenocarcinoma (GFP-MDA-MB-231) cells for 18 hours (C) magnified 10× by fluorescence (1000 ms exposure) and (D) under brightfield (1 ms exposure), respectively.
FIGS. 2E and 2F are images of 2% (w/v) barium alginate paper after culturing with green fluorescent protein-expressing human breast adenocarcinoma (GFP-MDA-MB-231) cells for 18 hours (E) magnified 10× by fluorescence (1000 ms exposure) and (F) under brightfield (1 ms exposure), respectively.

FIGS. 2A-2F are fluorescence microscopy images of a single layer of paper after culturing green fluorescent protein-expressing human breast adenocarcinoma (GFP-MDA-MB-231) cells. The GFP-MDA-MB-231 cells were cultured for 18 hours in Whatman 414 Filter Paper. FIGS. 2A and 2B are images of the Whatman 414 Filter Paper magnified 10× by fluorescence (1000 ms exposure) and under brightfield (1 ms exposure), respectively. The GFP-MDA-MB-231 cells were also cultured in barium alginate paper. FIGS. 2C and 2D are images of 0.5% (w/v) barium alginate paper magnified 10× by fluorescence (1000 ms exposure) and under brightfield (1 ms exposure), respectively. (FIGS. 2E and 2F are images of 2% (w/v) barium alginate paper prepared according to the method described in Example 1 (except a 2% (w/v) solution of Na alginate was used) magnified 10× by fluorescence (1000 ms exposure) and under brightfield (1 ms exposure), respectively.

Figure 3:
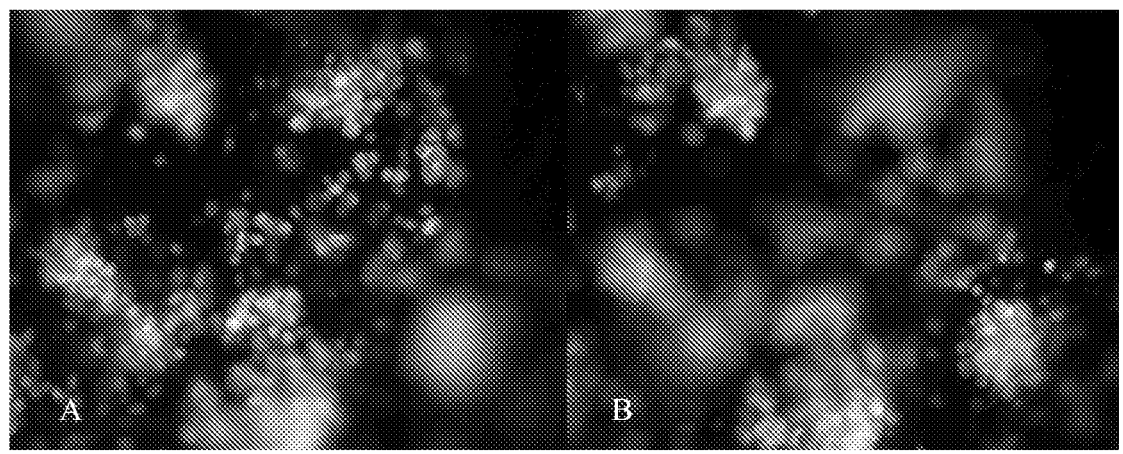
FIGS. 3A and 3B are fluorescence microscopy images of cultured GFP-MDA-MB-231 cells embedded in a single layer of 0.5% (w/v) barium alginate paper acquired at different focal planes corresponding to paper depths of (A) 0 μm and (B) 250 μm, respectively.

FIGS. 3A and 3B demonstrate the transparency of alginate paper, which can facilitate live cell imaging within a three-dimensional array. FIGS. 3A and 3B are fluorescence microscopy images of cultured GFP-MDA-MB-231 cells embedded in a single layer of 0.5% (w/v) barium alginate paper acquired at different focal planes corresponding to paper depths of 0 µm and 250 µm, respectively.

Barium alginate paper was prepared rapidly and cost-effectively on a multi-gram scale without using specialized laboratory equipment. Alginate hydrogel paper costs less than $0.01/cm$^2$, was prepared in minutes, and was amenable to manufacturing-scale preparation.

Example 2

The Preparation of Alginate Hydrogel Fiber with Protective Coating(s) of Positively-Charged and Negatively-Charged Polymer In this example, the preparation of representative alginate hydrogel fiber, barium alginate hydrogel fiber, with one or more protective coating(s) of positively-charged and negatively-charged polymer, is described.

Barium alginate fiber was fabricated by extruding 0.5% (w/v) sodium alginate through a needle into a bath of 0.5 M barium chloride. Next, the entangled fiber was rinsed with 0.05 M calcium chloride. The entangled fiber was added to a solution containing 0.05% (w/v) poly(diallyldimethylammonium chloride) and 0.05 M barium chloride. Poly(diallyldimethylammonium chloride) is a positively charged polymer with a molecular weight of 400 kDa. The entangled fiber was rinsed with 0.05 M calcium chloride. The entangled fiber was added to a solution containing 0.05% (w/v) sodium alginate. The sodium alginate is a negatively charged polymer with a molecular weight of 240 kDa. Next, the entangled fiber was rinsed with 0.05 M calcium chloride. One layer comprising one positively-charged polymer and one negatively-charged polymer was thus formed. These steps were repeated 2-12 times to create 1-6 layers, where each layer contained both a positively-charged and negatively-charged polymer. Increasing the number of layers can result in increased stability of the paper. For example, increasing from zero to three layers results in proportional stability of the paper.

Example 3

The Preparation of Alginate Hydrogel Fiber with Protective Coating(s) of Fibroin In this example, the preparation of barium alginate fibers with one or more protective coating(s) of fibroin is described.

Fibroin was used as a coating for the barium alginate paper fiber. Fibroin was prepared from the chemical degradation of silk cocoons, which was then followed by a dialysis step for purification that is well known in the art. Sheets of barium alginate paper were prepared, as described above, and the paper was coated with a dilute solution of fibroin, ranging from 0.05% to 5% (w/v). The coating was performed by submerging the paper into the fibroin solution for a defined period time, ranging from about 5 seconds to about 5 minutes. This step can be repeated depending on the number of coatings desired. The paper was then submerged into ethanol for 30 seconds. Submerging into ethanol sterilized the paper and cross-linked the fibroin, increasing the paper strength.

Example 4

Index-Matching Alginate Hydrogel Paper with Cell Culture Medium

In this example, the method of index-matching alginate hydrogel paper with cell culture medium is described.

Using a Bausch and Lomb Abbe Refractometer, the refractive index of cell culture medium was measured to be 1.3335. Alginate solutions with different alginate concentrations and different cation cross-linkers were prepared. The refractive indices of the different alginate solutions were measured. The refractive index of 0.5% (w/v) sodium alginate was measured to be 1.3335. The refractive index of 2.0% (w/v) sodium alginate was measured to be 1.3345. The refractive index of un-crosslinked sodium alginate approximates the refractive index of cross-linked barium alginate.

It was determined that 0.5% (w/v) sodium alginate and 2.0% (w/v) sodium alginate matched the index of refraction for cell culture medium. The 0.5% (w/v) sodium alginate solution and barium cation cross-linker solution were used to prepare alginate hydrogel paper that index-matched cell culture medium. The 2.0% (w/v) sodium alginate solution and barium cation cross-linker solution were also used to prepare alginate hydrogel paper that index-matched cell culture medium.

Other aspects, modifications, and embodiments are within the scope of the following claims.

What is claimed is:

1. A three-dimensional cellular array, comprising:
    an alginate hydrogel paper comprising:
        a plurality of alginate hydrogel fibers, comprising water in an amount of more than about 92% by weight of the fiber; and
        a cross-linked alginate in an amount of about 0.1% to about 8% by weight of the fiber, wherein the cross-link is a multivalent cation, and wherein the alginate hydrogel fibers form a woven or non-woven matrix; and
    a medium comprising cells, wherein the medium and cells are located in the hydrogel paper, wherein the alginate hydrogel making up the alginate hydrogel paper is substantially index-matched with the medium.

2. The cellular array of claim 1, wherein a selected region of the hydrogel paper comprises hydrogel and cells, and the hydrogel serves to support and contain the cells.

3. A three-dimensional cellular array, comprising:
    an alginate hydrogel paper comprising:
        a plurality of alginate hydrogel fibers, comprising water in an amount of more than about 92% by weight of the fiber; and
        a cross-linked alginate in an amount of about 0.1% to about 8% by weight of the fiber, wherein the cross-link is a multivalent cation, and wherein the alginate hydrogel fibers form a woven or non-woven matrix;
        wherein the alginate hydrogel paper comprises a plurality of porous regions, each porous region bounded at least in part by a liquid impervious boundary,
        wherein the alginate hydrogel making up the alginate hydrogel paper is substantially index-matched with an aqueous medium.

4. The cellular array of claim 1 or claim 3, wherein the array comprises a plurality of alginate hydrogel papers, and the plurality of the papers are arranged in a manner selected from the group consisting of in a stack, as a cascade, and as a loose web or loose net of fibers.

5. The cellular array of claim 4, wherein the array further comprises conventional paper.

6. The cellular array of claim 5, wherein the alginate hydrogel paper stack is disposed between a support framework.

7. The cellular array of claim 3, wherein the aqueous medium comprises cells disposed in the porous region.

8. The cellular array of claim 3, wherein the liquid impervious boundary is selected from the group consisting of siloxane, poly(lactic-co-glycolic acid), epoxy, polystyrene, a polyether, a polyamide, acrylate, polycarbonate, polyethylene, polypropylene, a photoresist precursor, a wax, and a fat.

9. The cellular array of claim 1 or claim 3, wherein the difference in refractive indices between the alginate hydrogel paper and the medium ranges from about 0.01 to about 0.

10. The cellular array of claim 1 or claim 3, wherein the cation cross-linker comprises barium.

11. The cellular array of claim 1 or claim 3, wherein the medium is selected from the group consisting of a biologically derived medium, nutrient medium, and simulated bodily fluid.

12. The cellular array of claim 1, wherein the alginate hydrogel paper is used to conduct analysis selected from the group consisting of a biochemical, diagnostic, cellular, and non-cellular analysis.

13. A method of conducting a cellular analysis, comprising:
   providing a three-dimensional cellular array according to claim 1 or claim 3; and a medium comprising cells, wherein the alginate paper is index matched with the medium, and wherein cells are located within a selected region of the cellular array; and
   visualizing the cells using light, wherein the alginate paper is translucent under the conditions used to visualize the cells.

14. The method of claim 13, wherein the visualization is carried out using a device selected from the group consisting of a fluorescent microscope, a light microscope, a fluorescent scanner, a light scanner, and a transmission spectrometer.

\* \* \* \* \*